United States Patent [19]

Cox

[11] 4,262,091

[45] Apr. 14, 1981

[54] PREPARATION OF CONTAMINANT FREE CONTAINERS OF CULTURE MEDIUM

[75] Inventor: Marion E. Cox, Cupertino, Calif.

[73] Assignee: Anaerobe Systems, Santa Clara, Calif.

[21] Appl. No.: 34,493

[22] Filed: Apr. 27, 1979

[51] Int. Cl.$^3$ ............................................. C12N 1/20
[52] U.S. Cl. ................................... 435/253; 435/31; 435/297; 435/299; 435/801; 435/810; 435/800
[58] Field of Search ............... 435/297, 298, 299, 809, 435/810, 801, 800, 243, 253, 254, 255, 240, 31, 311, 30; 312/1; 128/1 B, 1 R, 204

[56] References Cited

U.S. PATENT DOCUMENTS

| | | | |
|---|---|---|---|
| 2,244,082 | 6/1941 | Reyniers | 128/1 B |
| 2,862,307 | 12/1958 | Bloomer et al. | 128/1 B |
| 2,874,091 | 2/1957 | Fisk | 435/298 |
| 3,084,684 | 4/1963 | Saunders | 312/1 X |
| 3,775,256 | 11/1973 | Risinger | 435/801 X |
| 3,907,389 | 9/1975 | Cox et al. | 312/1 |
| 4,033,826 | 7/1977 | Larsen et al. | 435/801 X |
| 4,111,753 | 9/1978 | Folsom et al. | 435/801 X |

Primary Examiner—R. B. Penland
Attorney, Agent, or Firm—C. Michael Zimmerman

[57] ABSTRACT

A method and apparatus are described for providing petri dishes of a culture medium in an oxygen-free manner. Empty petri dishes are supplied to a dispensing glove box chamber providing isolation from the ambient atmosphere, by communicably connecting to such dispensing chamber, another glove box chamber providing isolation from the ambient atmosphere containing the empty dishes. The dishes are sequentially transferred to the dispensing chamber where they are filled with autoclaved culture medium. The filled dishes are transferred to a third chamber (also communicably connected to the dispensing chamber) within which the culture medium can solidify. Once the third chamber is filled with dishes having culture medium it is disconnected from the dispensing chamber and replaced with a fourth chamber having a new batch of unfilled petri dishes. The dishes from the new batch are then transferred into the dispensing glove box chamber and, once filled, transferred into the now empty chamber which provided the original batch of unfilled dishes. Each chamber containing filled petri dishes maintains such dishes in an isolated environment for a selected incubation period, and the dishes therein are then individually packaged in hermetically tight packages prior to being exposed to the ambient atmosphere.

8 Claims, 4 Drawing Figures

PREPARATION OF CONTAMINANT FREE CONTAINERS OF CULTURE MEDIUM

BACKGROUND OF THE INVENTION

The present invention relates to a method and apparatus for preparing containers of culture medium in isolation from an ambient atmosphere.

It is common clinical practice in identifying disease or the like, to grow a culture of bacteria removed from a patient. This is generally accomplished by inoculating a culture medium, such as an agar, with a sample of the bacteria of interest. The culture medium is contained within a petri dish or other container designed to hold the same for the growth of bacteria.

It is necessary for reliable results that the culture medium be free both of other bacteria which might grow and of any other contaminant which may either affect bacteria growth or make the results unreliable. That is, it is important that one know reliably that the bacteria which grows is a replication of the inoculated bacteria, and that there are no other contaminants within, on, or surrounding the culture medium which might adversely affect the growth of the bacteria of interest.

Petri dishes and other containers of culture medium are commonly prepared in the clinical laboratory in the ambient atmosphere. That is, the agar or other culture medium is placed in the dishes in the atmosphere prevailing in the laboratory. The culture medium often is provided in a dehydrated form and it is rehydrated at the time it is placed in the growth containers. Once filled, the petri dishes are generally transferred to protective chambers until such time as the medium is to be inoculated. It will be recognized that there is a chance the culture medium will be contaminated at the time it is rehydrated and placed in the the petri dishes. This problem is particularly acute with culture medium to be used to grow anaerobic bacteria, i.e., bacteria whose growth is inhibited by the presence of oxygen. The ambient atmosphere of a clinical laboratory will include oxygen, of course, and the rehydration of the medium and placement of the same in a petri dish in such atmosphere can result in oxygen contamination. There have been suggestions that this possibility can be obviated by rehydrating the media and placing it in containers in an isolated environment. In fact, small numbers of containers have been prepared in this way. However, it has not been practical until this time to prepare a large number of containers this way on a commercial basis. One problem is that humidity build-up in isolated environments often will cause deposition of water on the culture medium. The presence of water on a medium can materially affect its ability to sustain bacterial growth. Another problem is that until now there has not been a practical way to fill the containers continuously in an isolated environment. In this connection, glove box chambers have been proposed to be used. However, it typically requires a significant period of time to purge a glove box chamber of ambient atmosphere, and if the glove box chamber must be opened either to insert empty petri dishes or to remove filled ones, the purging cycle must be undergone before another batch of petri dishes can be filled.

Filled petri dishes and other containers are individually packaged and now provided commercially. However, because of the difficulties mentioned above, the dishes are neither prepared in an isolated, e.g., oxygen-free, environment nor packaged in a manner in which isolation is assured for a practical length of time.

SUMMARY OF THE INVENTION

It is therefore an object of the present invention to provide a method of preparing containers of a culture medium which assures the culture medium will not be contaminated. More particularly, it is an objct of the invention to provide such a method which enables petri dishes or other culture medium containers to be filled in an isolated atmosphere and to be maintained in such an atmosphere until such time as they are to be used. To this end, the invention comprehends dispensing the culture medium into containers therefor in a glove box chamber providing isolation from the ambient atmosphere. The filled containers, while still isolated from the environment, are placed within hermetically sealed packages prior to being exposed to the ambient atmosphere. The result is that individual containers of groups thereof can actually be prepared free of possible contamination at locations remote from the locations at which the bacteria is to be grown, and then maintained isolated for subsequent transportation and storage before use.

Most desirably, moisture is continuously removed from the interior of the glove box chamber during the step of dispensing culture medium into containers. This is most simply accomplished merely by passing the atmosphere of the glove box chamber continuously through an air conditioner. The formation of water on the surface of the culture medium in the individual containers, is therefore inhibited.

The empty petri dishes or other culture medium containers are preferably introduced into the dispensing glove box chamber from another chamber providing isolation from the ambient atmosphere, which is communicably connected with such glove box chamber. Once culture medium is dispensed within the empty containers, they are then most desirably transferred into a third chamber. This arrangement permits batch filling of the containers in a continuous manner. That is, after the third chamber has received a batch of filled containers, it can be detached from the dispensing chamber without requiring the latter chamber to be exposed to the ambient atmosphere.

Most desirably, a fourth chamber providing isolation from the ambient atmosphere is connected to the dispensing chamber in place of the third chamber. This fourth chamber preferably is filled with empty culture medium containers, and the container filling operation is then continued with containers from the new supply travelling in the reverse direction. That is, the empty containers are transferred into the dispensing chamber, have culture medium dispensed therein, and then placed in the first chamber—the chamber originally filled with empty containers. When the first chamber is filled with containers having culture medium it also can be detached from the arrangement and another chamber having empty containers placed in its position. The dispensing operation thus can be continued indefinitely, with the containers to be filled travelling alternately in opposite directions.

The invention includes other features and advantages which will be described or will become apparent from the following more detailed description of a preferred embodiment.

BRIEF DESCRIPTION OF THE DRAWINGS

With reference to the attached two sheets of drawing.

DETAILED DESCRIPTION OF A PREFERRED EMBODIMENT

The following description conforms to the manner in which the invention has been placed into practice by the inventor. It represents a description of the best mode contemplated by the inventor of carrying out his invention.

Figure 1:
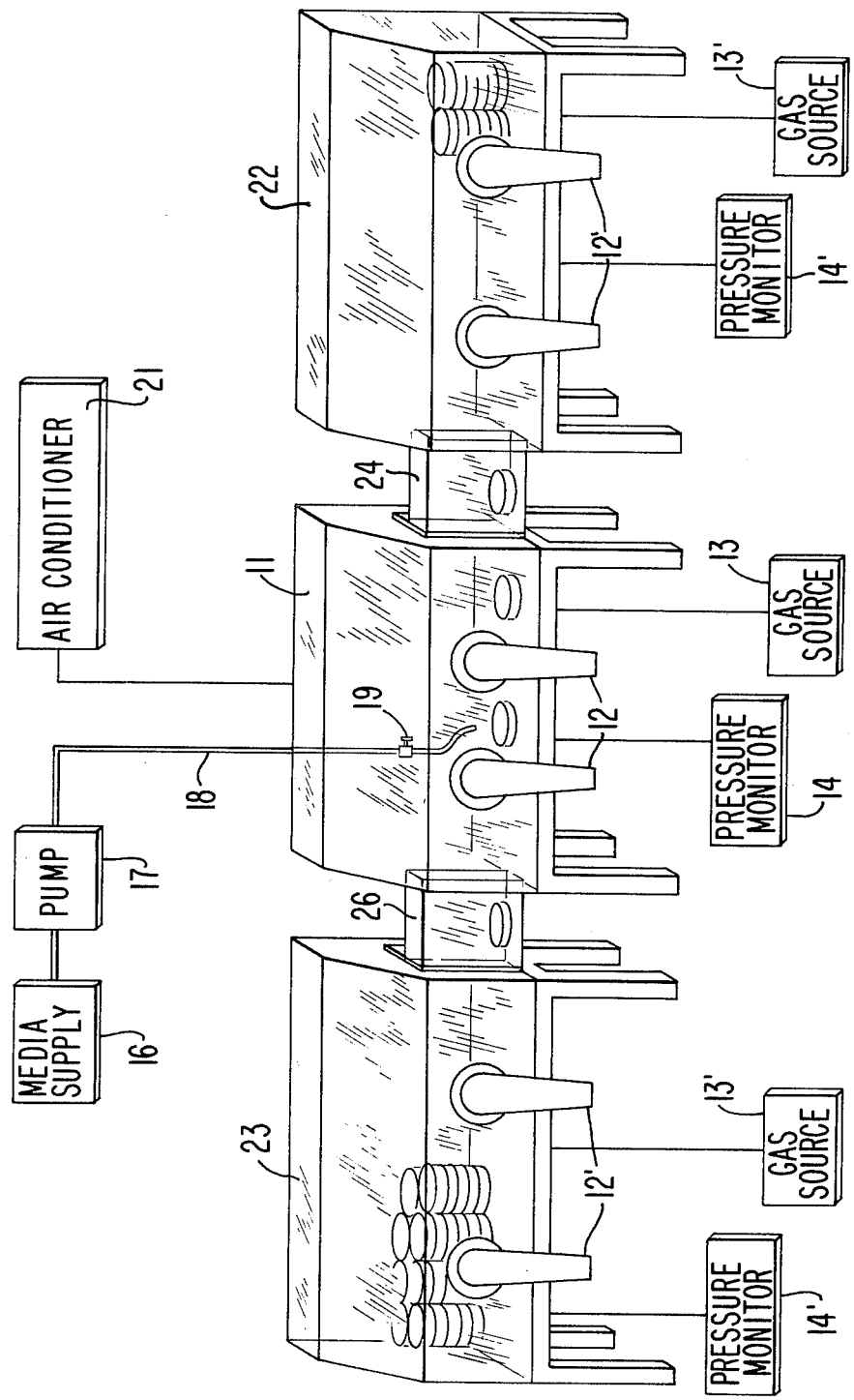
FIG. 1 is an isometric, partly schematic view of a preferred embodiment of the apparatus of the invention.

With reference to FIG. 1, the apparatus includes a glove box chamber 11 to provide isolation from a surrounding atmosphere. While any suitable glove box chamber could serve the purposes of the instant invention, most desirably chamber 11 is of the type described and claimed in U.S. Pat. No. 3,907,389, the disclosure of which is hereby incorporated by reference. In this connection, such chamber most desirably is one having rigid walls capable of maintaining a slight positive pressure with respect to the ambient atmosphere and having an opened ended sleeve-port arrangement of the type incorporated into the glove box chamber described in such patent to provide access to the chamber interior. Specifically, the walls of chamber 11 are formed from sheets of a rigid, transparent plastic, such as a rigid acrylic, and it includes a pair of flexible sleeves 12 surrounding associated access ports to provide preaccess chambers as defined in the aforementioned patent.

The preferred embodiment of the invention is particularly designed for packaging containers of culture medium to be used to grow anaerobic bacteria. Anaerobic bacteria are especially sensitive to contamination of the culture medium in view of their oxygen sensitivity. Thus, an essentially oxygen-free atmosphere is provided within the interior of the chamber 11. Such atmosphere could be provided in any of the conventional ways, such as by drawing a vacuum on the chamber or by flushing the same with an inert gas, such as nitrogen. It is preferred, however, that it be provided via catalytic conversion of the oxygen therein into water, for example, by introducing hydrogen in the presence of a catalyst into the chamber. A gas mixture of 90% nitrogen, 10% hydrogen has been found to be suitable when the catalyst is palladium. This provision of the gas mixture to the chamber is represented in FIG. 1 by the connection to the chamber of a block 13 labeled "gas source."

Most desirably, the pressure within the chamber 11 is maintained slightly positive with respect to atmospheric pressure so that any leakage flow will be from the chamber outward, rather than vice versa. Thus, a leak will not necessarily result in oxygen contamination of the chamber atmosphere. A pressure monitor, schematically represented at 14, is connected to the chamber to indicate the interior chamber pressure. In the event the pressure monitor shows that the pressure within the chamber is below that which is being provided, it will indicate a leak. The pressure monitor is therefore a leak indicator.

Means are included to dispense a culture medium within the glove box chamber. Such means is partly represented schematically in FIG. 1 by boxes 16 and 17 respectively, entitled "media supply" and "pump." Tubing 18 connected to the output of pump 17 passes suitably through the wall of chamber 11 to its interior, and has a pinch valve 19 on its end to permit control of flow of liquid media therethrough. The atmosphere within chamber 11 is continuously passed through an air conditioner as is represented by box 21, during the dispensing operation. Use of such air conditioner has two functions. For one, it maintains the temperature of the atmosphere within the glove box chamber at a suitably low level, e.g., about 65° F., to aid in the solidification of the culture media within the containers into which it is dispensed. In this connection, the culture medium typically is furnished as a powder, rehydrated, and then autoclaved. It is then furnished as a liquid (melted) to be pumped through tubing 18 and dispensed into petri dishes or other containers. The temperature of the medium when it is dispensed generally will be significantly higher than the temperature at which it is desired the atmosphere within the chamber 11 be maintained.

As another and important function, the air conditioner acts as means to dehumidify or, in other words, continuously remove moisture from, the interior of the glove box chamber. Introduction into the chamber of the liquid culture medium will result in the addition of moisture into the chamber environment, and it is important that such moisture be removed in order to assure good solidification of the culture medium without the formation of droplets of water on the medium surface later to be inoculated.

Communicably connected to glove box chamber 11 are second and third glove box chambers 22 and 23, respectively. Each of the chambers 22 and 23 also provides isolation from the ambient atmosphere. They are communicably connected to the glove box chamber 11 on opposite sides thereof by transfer passageways 24 and 26. Each of the passageways 24 and 26 is sized to permit passage therethrough of petri dishes or other containers to be filled with culture medium. However, each passageway is detachably connected at either one or both of its ends to the chamber adjoining the same at such end. That is, although for simplicity the detachable connection is not shown in any detail, each passageway is detachably connected at its ends to its adjoining chambers by suitable mechanism permitting detachment therefrom of the chamber without interfering with maintenance of the isolated atmospheres in the chambers and passageway. Any suitable detachment-connection construction could be used for this purpose. For example, the slide cover plate-slide rail arrangement for attaching containers to a chamber as described in the aforementioned patent could be adapted simply for this purpose. The transfer passageways 24 and 26 would take the place in such a construction of the container it is desired to be attached to the chamber. While it is preferable that each transfer passageway be detachable at both of its ends from the chambers between which it is situated, it will be recognized that in order to provide the desired disconnection of one glove box chamber from another it is only necessary that each passageway be designed to be disconnected at one of its ends from one of the chambers—it can be an integral part of one of the two chambers with which it is associated.

Because of the communication of the chambers 22 and 23 with chamber 11 provided by the transfer passageways 24 and 26, the three chambers cooperate when they are connected together to provide what is essentially a single, quite large chamber defining an oxygen-free atmosphere isolated from the ambient atmosphere. However, as will be discussed below, each of the chambers 22 and 23 will at some time during the process of the invention be detached from glove box chamber 11. Thus, the single, quite large chamber is separable into three sections within which isolated environments or atmospheres are maintainable. For this reason, chambers 22 and 23 are shown provided with their own gas sources and pressure monitors 13' and 14', respectively.

In performing the method of the invention, the culture medium dispensed within the containers is itself most desirably provided in the manner which minimizes the possibility of contamination. Culture medium, such as agar, typically is furnished as a dehydrated powder in sealed packages. In carrying out the invention, the medium in its dehydrated form is placed with a proper amount of water for rehydration in a suitable container which can be hermetically sealed and autoclaved. After the medium is placed within such a container, the container is sealed and flushed free of ambient atmosphere with a suitable gas, such as nitrogen. From this point, the medium will be maintained anaerobic throughout the remaining steps of the process. The batch of culture medium is then autoclaved while it is retained within the sealed container, to kill any extraneous bacteria associated therewith. For example, it is brought to a temperature of about 121° C. for around 15 minutes for this purpose. Once it is autoclaved, it is then cooled to a relatively low dispensing temperature, e.g. 46° C. for agar, and any desired heat labile supplements are then added. The batch of medium is then ready to be dispensed into containers therefor of the type within which medium is supported during the growth of bacteria, e.g., petri dishes.

Before chamber 22 is communicably connected to glove box chamber 11, it is filled with empty petri dishes or other containers for culture medium. It is then individually hermetically sealed and provided with an anaerobic atmosphere in a manner discussed previously for chamber 11. When the interior of such chamber has an oxygen-free atmosphere, it is communicably connected via the passageway 24 to chamber 11. Chamber 23 may or may not at such time already be connected to the other end of chamber 11. If it is not, the isolated environment defined by the same is made oxygen-free if necessary, and it is thereafter communicably connected to chamber 11 via passageway 26.

It should be noted that whereas chamber 22 is filled with a plurality of empty petri dishes, chamber 23 includes room to receive containers after they are filled with culture medium—chamber 23 preferably is empty of dishes.

Once a batch of culture medium to be dispensed is prepared as described above and the chambers 22 and 23 are connected to chamber 11, the dispensing operation is ready to be commenced. That is, empty petri dishes from chamber 22 are transferred to glove box chamber 11; have culture medium dispensed therein via pump 17, tube 18, and valve 19; and are then transferred to chamber 22 to solidify. Since chambers 22 and 23 are glove box chambers, direct access can be made thereto for manipulation of the containers to transfer empty ones into the dispensing chamber 11 and to stack filled ones in the chamber 23.

While dispensing is taking place, the air conditioner 21 is operating so that any moisture which otherwise would build up in the interior of chamber 11 will be continuously removed from the chamber atmosphere. Moreover, the atmosphere within the chamber 11 and, of course, within the chambers 22 and 23 is maintained during such time essentially oxygen-free.

Figure 2:
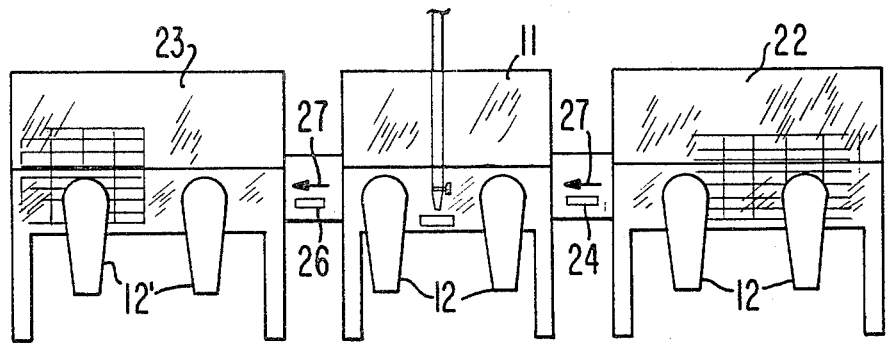
FIGS. 2 and 3 are schematic views of the relationship of isolation chambers to one another during practice of the method of the invention.

The dispensing operation continues repeatedly in a sequential manner. That is, one or more dishes transferred to the chamber 11 are filled and then transferred to the chamber 23 before additional dishes are transferred from chamber 22 into chamber 11. This sequence of operation is schematically represented in FIG. 2 by the arrows 27 at the passageways between the chambers. It has the advantage of separating the work area from the supply of empty dishes and the dishes having solidifying culture medium. Thus, the likelihood of the presence of empty and filled petri dishes interferring with the dispensing operation is minimized.

As a particularly salient feature of the method of the invention, it includes a sequence of steps resulting in each end chamber serving several functions. As represented in FIG. 2 by arrow 28, when chamber 23 is filled with petri dishes containing culture medium, it is disconnected from chamber 11. In this connection, it is disconnected without its oxygen-free atmosphere becoming contaminated. Such chamber then is used to maintain the filled petri dishes isolated from the ambient atmosphere under bacteria growth inducing conditions for a selected incubation period. The purpose of such incubation is to discover prior to packaging, whether or not any of the petri dishes may contain contamination bacteria. That is, the chamber is maintained for a period of about 24 hours at a temperature of around 35° C. to assure that the medium is sterile and that all steps in the dispensing operation were accomplished in an aseptic manner.

Figure 3:
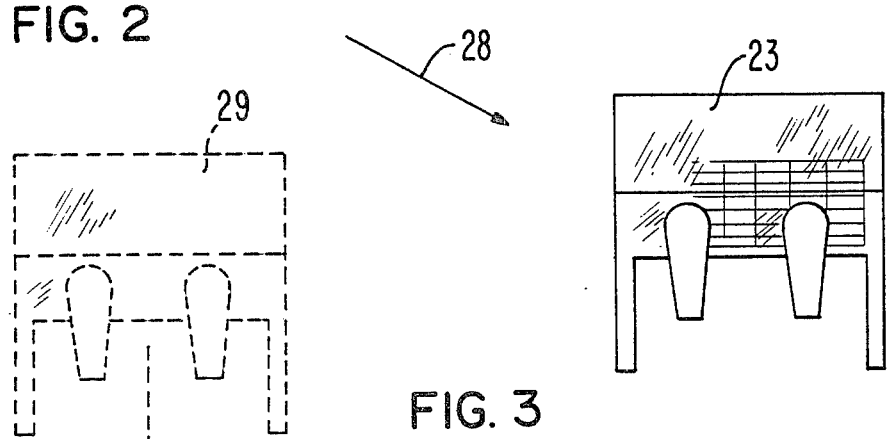
Figure 4:
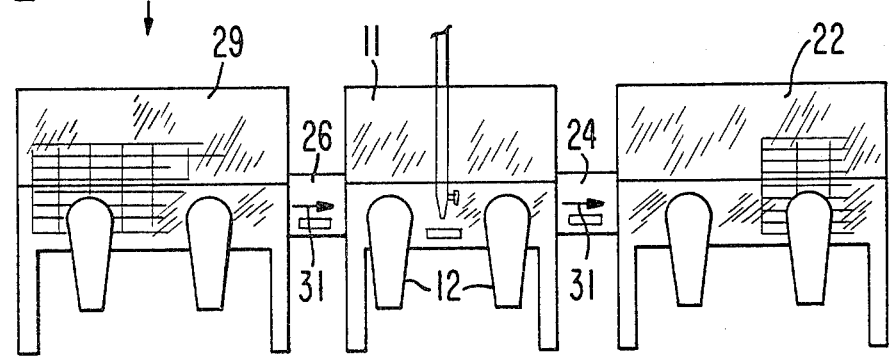
FIG. 4 is an isometric view of a petri dish package provided in accordance with the method of the invention.
Figure 4:
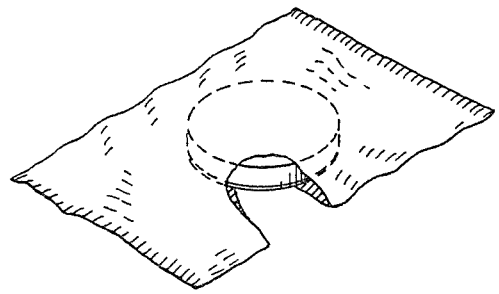

When chamber 23 is disconnected from chamber 11, it is replaced by a fourth chamber having unfilled petri dishes. This replacement is represented in FIG. 3 by the phantom showing of chamber 29 and movement thereof to a position communicably connected to chamber 11 via passageway 26. The operation of dispensing medium into containers in an isolated environment can then be continued by transferring the unfilled dishes in chamber 29 into dispensing chamber 11, dispensing medium therein, and then transferring the filled chambers into chamber 22. In this connection, if all of the unfilled dishes originally in chamber 22 have been transferred to chamber 11 and have medium dispensed therein, chamber 22 will be empty of dishes but will continue to be communicably connected to the chamber 11 and provide the same atmosphere as chamber 11. Thus, chamber 22 serves two different functions when it is connected to chamber 11, i.e., it serves to furnish petri dishes for the dispensing operation and subsequently to receive filled petri dishes. It should be noted that the direction of flow of the petri dishes then being filled indicated by the arrow 31 in FIG. 3 is opposite to the direction of petri dish flow indicated by the arrow 27 in FIG. 2.

The operation of dispensing can thus continue indefinitely subject, of course, to the availability of medium to dispense. That is, merely by alternating the direction of flow of the petri dishes, the dispensing operation can continue only interrupted by the time involved in replacing one end chamber containing filled petri dishes with one having empty petri dishes. In this sense, the process is a continuous "batch" process. It is a "batch" process in that discrete batches of dishes are filled. It is a continuous process, however, in that by periodically providing as required chambers filled with empty containers and removing chambers with filled containers, the dispensing operation within chamber 11 can be carried on continuously.

After the filled dishes in chamber 23, for example, have been incubated for a sufficiently long time to assure that they are aseptic, they are then ready to be individually packaged for transportation and storage before use. This can be simply accomplished by communicably connecting chamber 23 to another glove box chamber providing a packaging work station. Such a chamber has essentially the same attributes as chamber 11, except that rather than a dispensing means, it includes suitable packaging mechanism. In this connection, the packaging station glove chamber is also provided with an essentially oxygen-free atmosphere and moisture is continuously removed therefrom by air conditioning or other means.

Most desirably, the individual dishes are separately packaged in flexible packaging material of the type having, for example, a laminant of aluminum foil for oxygen impermeability sandwiched between outside laminants of a heat sealable material, such as polyethylene. The packaging for each petri dish is most simply provided as an individual envelope which is closed on three sides, but has an open end enabling insertion of a filled dish.

The envelopes can be introduced into the isolated environment of the packaging glove box chamber in numerous ways. For example, a supply of empty envelopes can be placed in each end chamber at the same time the chamber is filled with empty petri dishes. There should be enough envelopes in the supply to package all of the filled petri dishes which subsequently will be placed into the chamber during the dispensing operation. This will assure the availability of the envelopes in the isolated packaging environment, without the necessity of using pass boxes or passthroughs to introduce the envelopes into such environment along with the filled petri dishes.

Once the chamber having the filled petri dishes and the empty envelopes is communicably connected with the packing station chamber, the packaging operation can be completed. That is, each of the filled dishes and an envelope therefor are transferred to the packaging station, assembled, and then the package is closed by heat sealing with a commercially available heat sealing mechanism. The package can then be transferred out of the glove box for subsequent exposure to the ambient atmosphere. The latter transferrence for exposure to the ambient atmosphere can take place a couple of different ways. For example, an end chamber can be communicated with the packaging station chamber on the side thereof opposite the side of the chamber providing the filled dishes to be packaged. The packaged dishes can then be transferred to such end chamber after the packaging operation, which end chamber, once filled, can be disconnected from the packaging glove box chamber. Such end chamber can then be exposed to the ambient atmosphere and the packaged dishes removed. The chamber is then available to be filled with empty dishes (and envelopes if desired) and provided again with an oxygen-free atmosphere for connection to dispensing glove box chamber 11.

Alternatively, it is contemplated that the packaging chamer itself include a passthrough to the ambient atmosphere which permits the packaged dishes to be directly emitted into the ambient atmosphere, without permitting the ambient atmosphere to adversely affect the isolation provided by the packaging chamber. Such an arrangement has the advantage of obviating the necessity of connecting and then disconnecting a receiving chamber to the main packaging chamber.

Although the invention has been described in connection with preferred embodiments thereof, it will be appreciated by those skilled in the art that various changes and modifications can be made without departing from its spirit. For example, as described, each package holds only a single petri dish. It will be recognized, however, that separate packages could be provided with each holding a greater number of petri dishes. Moreover, although it has been described with petri dishes being exemplary of the containers to be packaged, the invention is applicable to preparing in isolation from an ambient atmosphere, any kind of a container of culture medium. In view of these and other potential changes, it is intended that the coverage afforded applicant be limited only by the terms of the claims and their equivalent language.

I claim:

1. A method of preparing containers of culture medium in isolation from oxygen, comprising:

connecting the interior of a hermetic glove box chamber providing isolation from an ambient atmosphere and having means to dispense a culture medium, with the interior of a second hermetic chamber having a plurality of empty culture medium containers therein;

connecting the interior of said glove box chamber with the interior of a third hermetic chamber to receive containers of culture medium;

providing an essentially oxygen-free atmosphere within the interiors of said glove box, said second chamber and said third chamber;

transferring empty culture medium containers from said second chamber to said glove box chamber;

dispensing culture medium into said containers from said second chamber while said containers are in said glove box chamber and while maintaining an essentially oxygen-free atmosphere within said glove box;

continuously removing moisture from the interior of said glove box chamber while dispensing said culture medium into said containers from said second chamber;

transferring containers having culture medium from said glove box into said third chamber while maintaining an essentially oxygen-free atmosphere in said third chamber;

connecting the interior of said glove box chamber with a fourth hermetic chamber having a plurality of empty culture medium containers therein;

transferring empty culture medium containers from said fourth chamber to said glove box chamber;

dispensing culture medium into said containers from said fourth chamber while said containers are in said glove box chamber and while maintaining an essentially oxygen-free atmosphere within said glove box;

continuously removing moisture from the interior of said glove box chamber while dispensing said culture medium into said containers from said fourth chamber; and thereafter transferring said containers from said fourth chamber into said second chamber while maintaining an essentially oxygen-free atmosphere in said second chamber whereby medium containers are batch filled in a continuous manner.

2. A method according to claim 1 wherein said containers provided within said second and fourth chambers are petri dishes for supporting the growth of bacteria.

3. A method according to claim 1 wherein said second, third and fourth chambers are glove box chambers to facilitate manipulation therein of said containers.

4. A method according to claim 1 further including after said step of transferring containers from said glove box chamber into said third chamber, the steps of:

disconnecting said third chamber from said glove box chamber while maintaining the interior of said third chamber essentially oxygen-free;

maintaining the interior of said third chamber isolated from said ambient atmosphere for a selected incubation period; and thereafter sealing said containers, in hermetic packages prior to exposing said containers to said ambient atmosphere, thereby provided a plurality of separate packages of said containers having culture medium isolated from said ambient atmosphere for separate transportation and storage.

5. A method of preparing containers of culture medium in isolation from oxygen, comparising:

autoclaving culture medium suitable for the growth of anaerobic bacteria, in an essentially oxygen-free atmosphere;

providing a glove box chamber having an interior isolated from an ambient atmosphere and having means to dispense a culture medium therein;

providing an essentially oxygen-free atmosphere within the interior of said glove box chamber;

placing in said glove box chamber a plurality of empty containers for said culture medium;

dispensing said culture medium into said containers while said containers are in said glove box chamber and maintaining an essentially oxygen-free atmosphere therein;

continuously removing moisture from the interior of said glove box chamber while dispensing said culture medium into said containers; and sealing said containers while they are maintained in an essentially oxygen-free atmosphere and prior to being exposed to said ambient atmosphere, in packages which essentially are oxygen impervious thereby providing a plurality of separate packages of said containers having culture medium isolated from oxygen and from said ambient atmosphere for separate transportation and storage.

6. A method according to claim 5 wherein said step of placing in said glove box chamber a plurality of empty containers includes the step of:

connecting the interior of said glove box chamber with a second hermetic chamber having a plurality of empty culture medium containers therein;

providing an essentially oxygen-free atmosphere within the interior of said second chamber; and transferring to said glove box chamber from said second chamber, empty culture medium containers.

7. A method according to claim 6 further including prior to sealing said containers in hermetic packages the steps of:

connecting the interior of said glove box chamber with a third, hermetic chamber to receive containers of culture medium;

providing an essentially oxygen-free atmosphere within the interior of said third chamber;

transferring said containers having culture medium from said glove box chamber into said third chamber; and maintaining the interior of said third chamber essentially oxygen-free and isolated from said ambient atmosphere for a selected incubation period.

8. A method according to claim 7 further including the steps of:

disconnecting said third chamber from said glove box chamber while maintaining the interior of said third chamber essentially oxygen-free;

connecting the interior of said glove box chamber with a fourth hermetic chamber having a plurality of empty culture medium containers therein;

transferring empty culture medium containers from said fourth chamber to said glove box chamber;

dispensing culture medium into said empty containers from said fourth chamber while said containers are in said glove box chamber and while maintaining an essentially oxygen-free atmosphere therein; and thereafter transferring said containers from said fourth chamber into said second chamber while maintaining an essentially oxygen-free atmosphere in said second chamber.

* * * * *